(12) United States Patent
Sugawara et al.

(10) Patent No.: US 9,351,934 B2
(45) Date of Patent: May 31, 2016

(54) CROSSLINKED GELATIN SUPPORT AND SUPPORT FOR CONTROLLED RELEASE OF PHYSIOLOGICALLY ACTIVE SUBSTANCE USING THE SAME

(71) Applicant: NITTO DENKO CORPORATION, Ibaraki-shi, Osaka (JP)

(72) Inventors: Shinji Sugawara, Osaka (JP); Chieko Miura, Osaka (JP); Tomoko Sudo, Osaka (JP); Masao Nakagawa, Osaka (JP); Toshiyuki Yoshikawa, Osaka (JP)

(73) Assignee: NITTO DENKO CORPORATION, Osaka (JP)

( * ) Notice: Subject to any disclaimer, the term of this patent is extended or adjusted under 35 U.S.C. 154(b) by 0 days.

(21) Appl. No.: 14/256,134

(22) Filed: Apr. 18, 2014

(65) Prior Publication Data

US 2014/0316013 A1    Oct. 23, 2014

(30) Foreign Application Priority Data

Apr. 22, 2013 (JP) ................. 2013-089142
Apr. 22, 2013 (JP) ................. 2013-089143

(51) Int. Cl.
    *A61K 9/16*    (2006.01)
(52) U.S. Cl.
    CPC ............. *A61K 9/1676* (2013.01); *A61K 9/1658* (2013.01)
(58) Field of Classification Search
    CPC .................................................. A61K 9/1676
    See application file for complete search history.

(56) References Cited

U.S. PATENT DOCUMENTS

2004/0253294 A1*  12/2004  Tabata .................... 424/426
2011/0229580 A1    9/2011  Srivastava et al.

FOREIGN PATENT DOCUMENTS

| EP | 1 415 663 A1 | 5/2004 |
| EP | 1 555 030 A1 | 7/2005 |
| JP | 3879018 B2 | 2/2007 |

OTHER PUBLICATIONS

Extended European Search Report dated Jun. 6, 2014 issued by the European Patent Office in counterpart European Patent Application No. 14165440.0.
Kenneth Ofokansi et al; "Matrix-loaded biodegradable gelatin nanoparticles as new approach to improve drug loading and delivery"; European Journal of Pharmaceutics and Biopharmaceutics; XP027210077; vol. 76, No. 1, Sep. 1, 2010, pp. 1-9.
J. Vandervoort, et al; "Preparation and evaluation of drug-loaded gelatin nanoparticles for tropical ophthalmic use"; European Journal of Pharmaceutics and Biopharmaceutics; XP027139982; vol. 57, No. 2, Mar. 1, 2004; pp. 251-261.
Sushma Kommareddy, et al; "Preparation and Evaluation of Thiol-Modified Gelatin Nanoparticles for Intracellular DNA Delivery in Response to Glutathione"; Bioconjugate Chemistry; XP002543454; vol. 16, No. 6, Nov. 1, 2005; pp. 1423-1432.

\* cited by examiner

*Primary Examiner* — Paul Zarek
(74) *Attorney, Agent, or Firm* — Sughrue Mion, PLLC

(57) ABSTRACT

The present invention relates to a crosslinked gelatin support, in which a surface of a crosslinked gelatin is negatively charged and has a zeta potential in ethanol of from −3 to −50 mV, and a support for controlled release of a physiologically active substance, including: the crosslinked gelatin support; and a physiologically active substance adsorbed and retained on and/or inside the crosslinked gelatin support.

5 Claims, 1 Drawing Sheet

CROSSLINKED GELATIN SUPPORT AND SUPPORT FOR CONTROLLED RELEASE OF PHYSIOLOGICALLY ACTIVE SUBSTANCE USING THE SAME

FIELD OF THE INVENTION

The present invention relates to a crosslinked gelatin support and a support for controlled release of a physiologically active substance using the same. Specifically, the invention relates to a crosslinked gelatin support having a negative charge zeta potential in which surface charge of the crosslinked gelatin formed of particles or the like is from −3 to −50 mV, particularly a crosslinked gelatin support formed of particles or the like in which a content of water-soluble matter is controlled to a specific range, and a support for controlled release of a physiologically active substance in which a physiologically active substance is adsorbed and retained on the support.

BACKGROUND OF THE INVENTION

Gelatin is a protein obtained by a treatment of animal-derived collagen with an acid or alkali and subsequent extraction and is a familiar material which is utilized in various fields, for example, is used as a gelling agent in food fields such as jelly, pharmaceutical fields, and the like and is also used in industrial uses such as adhesive and film fields. Of these various uses, highly purified gelatin and collagen used in medical uses are listed also in the Japanese Pharmacopoeia and have been widely utilized as an additive for injection preparations and in products such as an embolic material for liver cancer, a sponge material for hemostasis, and a capsule material for oral administration.

As mentioned above, since gelatin is extracted from collagen that constitutes biological tissues, gelatin is a material extremely excellent in biocompatibility and biodegradability. Furthermore, gelatin usually has a property of relatively easily dissolving in water and warm water and, by subjecting gelatin to a crosslinking treatment to thereby achieve insolubilization and controlling a degree of insolubilization, has a property that a biodegradation time of gelatin can be controlled at the time when it is administrated to a living body. Therefore, when a physiologically active substance such as a drug is previously adsorbed to a crosslinked and insolubilized gelatin, in the case where it is administrated to a living body, the physiologically active substance can be gradually released along with dissolution of gelatin by biodegradation, so that an action of controlled releasing of the physiologically active substance over a certain period of time can be exhibited.

Patent Document 1 discloses an invention in which gelatin as a biocompatible substance is made water-insoluble and is transformed into a porous particle and there is a description that the particle is useful for embolization treatment and as a support for medical preparations. Namely, the water-insolubilized porous particle is impregnated in its porous part with physiological saline or a solution of a pharmaceutical or the like and retains it. However, since the impregnation and retention are achieved in its porous part, for example, the adsorbed amount thereof is varied to a large extent when the pore diameter and the porosity are changed, so that there is a problem that it is difficult to control the adsorbed amount.

Patent Document 1: Japanese Patent No. 3879018

SUMMARY OF THE INVENTION

Usually, in the case where, after a physiologically active substance such as a drug is previously adsorbed to a crosslinked gelatin and is suspended with physiological saline or the like, the gelatin is administrated to a living body to achieve controlled release of the physiologically active substance, it becomes important to control and regulate the adsorbed amount of the physiologically active substance in the crosslinked gelatin depending on the prescription and therapeutic purpose of the physiologically active substance.

However, when the crosslinked gelatin support does not have an adsorbed amount of the physiologically active substance necessary for therapy or the like, there arise problems that an effective therapeutic effect cannot be exhibited even if the support is administrated to the living body and also the controlled release of the physiologically active substance cannot be achieved over a desired period of time.

As a result of preparing a crosslinked gelatin capable of regulating a biodegradation time in a living body and performing investigation of causes that influence the adsorbed amount of the physiologically active substance for solving the above problems, the present inventors have found that surface charge of the crosslinked gelatin remarkably influences the adsorbed amount and the content of water-soluble matter in the crosslinked gelatin strongly influences the adsorbed amount. Thus, they have accomplished the invention.

Namely, the invention provides a crosslinked gelatin support, in which a surface of a crosslinked gelatin is negatively charged and has a zeta potential in ethanol of from −3 to −50 mV.

Particularly, the crosslinked gelatin is preferably not one subjected to a chemical crosslinking treatment with a common chemical crosslinking agent or the like but one physically crosslinked by a thermal treatment. More preferred is one subjected to a decomposition treatment by further performing a γ-ray irradiation treatment after the crosslinking treatment.

Moreover, it is preferred that a content of a water-soluble matter in the crosslinked gelatin support before the decomposition treatment is from 15 to 50% by weight and is increased to 25 to 75% by weight after the decomposition treatment. Additionally, it is preferred that the crosslinked gelatin support is a single particle having a non-porous structure or a particle aggregate thereof.

Furthermore, the invention can provide a support for controlled release of a physiologically active substance, which is excellent in ability of controlled release, by adsorbing and retaining a physiologically active substance on and/or inside the crosslinked gelatin support mentioned above.

The crosslinked gelatin support of the invention exhibits an effect that the adsorbed and retained amount of a physiologically active substance can be accurately regulated by controlling the surface charge to negative charge, specifically controlling the zeta potential in ethanol to a range of −3 to −50 mV. Therefore, by changing the surface charge of the crosslinked gelatin support within a specific zeta potential range, a support for controlled release can be obtained, which achieves controlled release of a physiologically active substance so as to exhibit a desired therapeutic effect.

Moreover, the crosslinked gelatin support of the invention exhibits an effect that the adsorbed and retained amount of a physiologically active substance can be accurately regulated by controlling the content of water-soluble matter in the crosslinked gelatin support before and after the decomposition treatment so as to increase the content in a specific range. Namely, since the amount of the water-soluble matter in the crosslinked gelatin support is controlled and changed so as to be in a specific range before and after the decomposition treatment, it is possible to obtain a support for controlled release, which achieves controlled release of a physiologically active substance so as to exhibit a desired therapeutic effect.

DETAILED DESCRIPTION OF THE INVENTION

Figure 1:
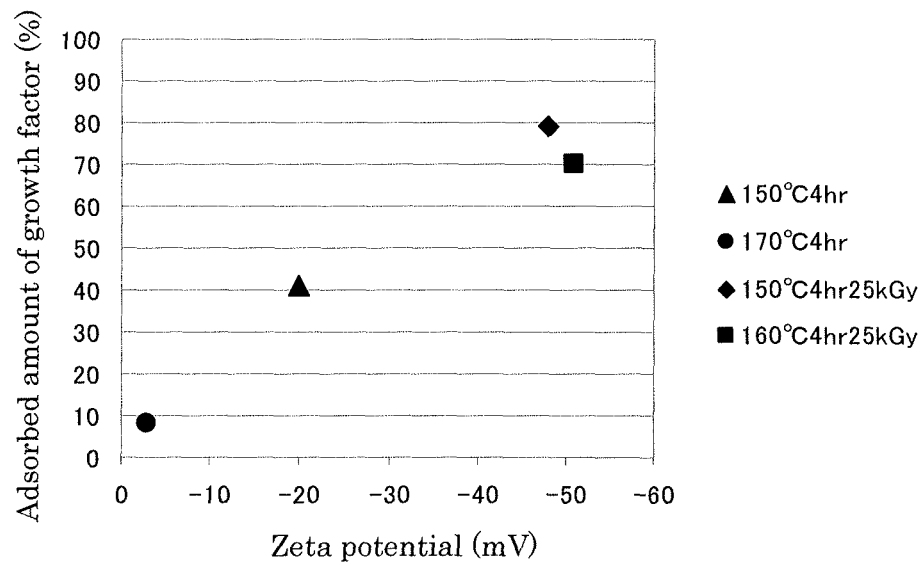
FIG. 1 is a graph showing relationship between the surface charge (zeta potential) of the crosslinked gelatin support obtained in each of Examples 1 to 3 and Comparative Example 1 and the adsorption ratio of growth factor as a physiologically active substance.

With regard to the gelatin to be used in the invention, the kind (source) thereof is not particularly limited. For example, various gelatins derived from bovine bone, bovine skin, swine bone, swine skin, and the like can be used.

The crosslinked gelatin support of the invention is one obtained by subjecting gelatin shaped into particles to a crosslinking treatment for insolubilization against aqueous solvents and preferably, is one not subjected to a commonly used chemical crosslinking treatment with a crosslinking agent but desirably subjected to thermal crosslinking by a heating treatment. Namely, in the case where the chemical crosslinking treatment with a crosslinking agent is performed, there is a possibility that a reaction product of the crosslinking agent or a residue of the crosslinking agent is bonded to gelatin. In the case where the thus obtained crosslinked gelatin support is used in a living body, various kinds of toxicity and the like should be carefully investigated and there arises a limitation on usable crosslinking agents.

On the other hand, in the case where thermal crosslinking is performed by the heating treatment, there is absent any concern like the above and the crosslinking treatment is performed under mild conditions as compared with the crosslinking treatment with a crosslinking agent, so that regulation of the degree of crosslinking of gelatin that influences biodegradability becomes relatively easy. Therefore, in the case where the crosslinked gelatin support is prepared by thermal crosslinking as in the invention, since the degree of crosslinking can be controlled depending on the intended purpose, a time for complete dissolution in an aqueous solution or a blood vessel (biodegradation time or the like) can be easily controlled.

In order to obtain the crosslinked gelatin support of the invention as a particle shape, first, a particle-shaped gelatin support can be made by a known granulation method such as a W/O dispersion method, a microreactor method, a spray dry method, a spray freeze-dry method, or a pulverization method.

Then, the resulting gelatin support is once dried by means of a drying method such as blow drying, air drying, vacuum drying, or freeze drying and subsequently heated and dried at a temperature range of 100 to 200° C., preferably 120 to 180° C., for 2 to 48 hours, preferably 2 to 8 hours, whereby thermal crosslinking is performed to result in the crosslinked gelatin support of the invention. However, in the case of not heating and drying under standing but heating and drying under stirring or rotation conditions, it is preferable to perform the heating treatment at a temperature range of 150 to 170° C.±5° C. for about 3 to 5 hours. On this occasion, drying may be performed under normal pressure but, since gelatin that is intrinsically water-soluble and is easily influenced by oxygen, moisture, and the like in the air, a heating treatment under vacuum is preferable for performing homogeneous thermal crosslinking with good reproducibility. The "under vacuum" in the invention means a pressure condition of 10 kPa or less which can be achieved by a usual vacuum drier, when absolute vacuum is taken as 0 kPa.

Moreover, the crosslinked gelatin support in the invention can be also obtained by performing a decomposition treatment after the crosslinking treatment as described above is performed. In the crosslinked gelatin support thus subjected to the decomposition treatment, since the negative charge on the support surface can be further increased by the decomposition treatment, the zeta potential on the support surface effective for adsorption of a physiologically active substance can be controlled to a desired value within a range of −3 to −50 mV, so that the support is preferable. Furthermore, by keeping balance between water-insolubilization of gelatin by the crosslinking treatment and re-solubilization in water of the water-insolubilized gelatin by the decomposition treatment, the adsorbed amount of a physiologically active substance can be controlled.

As the decomposition treatment in the invention, there may be mentioned a decomposition treatment by irradiation with radiation including γ-ray, irradiation with electron beam, or the like. Preferably, it is practically desirable to use γ-ray that can be also utilized as a final sterilization treatment after product packaging. The irradiation quantity of γ-ray is preferably about from 10 to 50 kGy, but an irradiation quantity ranging from 25 to 50 kGy, which can be sufficiently accommodated also as a sterilization operation, is further preferable in view of controlling the zeta potential on the surface of the crosslinked gelatin support and decomposing the water-insolubilized crosslinked gelatin to make it surely water-soluble.

In the crosslinked gelatin support of the invention obtained as above, the structure of inside of the support is not particularly limited but it is preferable that the surface zeta potential can be easily controlled and the content of the water-soluble matter can be easily controlled by controlling the crosslinking treatment or the decomposition treatment. When the point is considered, the control becomes difficult in a porous structure since control of the surface area at the pore part is also necessary, so that it is preferable to be a particle having a non-porous structure and further preferably, a single particle having a non-porous structure or a particle aggregate obtained by aggregation of a plurality of particles thereof is desirable.

Namely, when the support is a particle having a porous structure, the specific surface area becomes large and the surface charge in the porous part inside the particle also influences the effect of the invention, so that a desired surface zeta potential as the crosslinked gelatin support becomes difficult to control and the adsorbed amount (retained amount) of a physiologically active substance tends to be difficult to set to a desired value. Furthermore, when the support is a particle having a porous structure, since the surface part in the pore part also influences water-solubility by the decomposition treatment and physical adsorption of the physiologically active substance also takes place due to a capillary phenomenon to the pore part, a large influence is exerted on the effect of the invention, i.e., adsorbability control of the physiologically active substance and thus there is a tendency that the desired effect is difficult to obtain surely with good reproducibility. Therefore, in order to surely exhibit the effect of the invention, it is preferable to use a gelatin particle having a non-porous structure.

Moreover, in the resulting crosslinked gelatin support, it is desirable that the average particle diameter of single particle of the crosslinked gelatin at a dried state is from 5 to 50 μm, preferably from 5 to 25 μm, from the standpoint of controlling the zeta potential within the range of the invention to make the control of the adsorbed amount of the physiologically active substance possible. When the average particle diameter is less than 5 μm, since the particle is too small, biodegradability is increased in the case of introducing it into a living body and the effect of the invention is difficult to exhibit sufficiently. Therefore, there arises a necessity for severe crosslinking conditions for performing further crosslinking and the zeta potential is transferred to a neutral side, so that there is a tendency that the effect of the invention is not sufficiently obtained. On the other hand, in the case where the average particle diameter exceeds 50 μm, the charge inside the particle also influences the effect of the invention and the control of the zeta potential so as to exhibit the effect of the invention as the crosslinked gelatin support tends to be difficult, so that the case is not preferable.

However, from the standpoint of performing the crosslinking treatment and the decomposition treatment uniformly on the whole gelatin particle, it is desirable that the average particle diameter of single particle of the crosslinked gelatin support at a dried state is from 25 to 2,000 μm, preferably from 60 to 1,700 μm. In the case where the average particle diameter is less than 25 μm, since the particle is small, the regulation of amount of the water-soluble matter becomes difficult and also, for example, in the case where the crosslinked gelatin support of the invention is introduced into a living body, there is a tendency that biodegradability is exceedingly increased and the effect of the invention is difficult to exhibit sufficiently. In this regard, when further crosslinking is intended to perform for the purpose of decreasing the biodegradability, there arises a necessity of severe crosslinking conditions, so that a sufficient amount of the water-soluble matter cannot be obtained even when the decomposition treatment is performed. As a result, the effect of the invention is not sufficiently obtained. On the other hand, in the case where the average particle diameter exceeds 2,000 μm, a uniform crosslinking treatment is difficult to perform on the whole gelatin particle and also the decomposition treatment is effected partially on a surface layer part alone. As a result, the control of the biodegradability becomes difficult to perform and there is a tendency of exerting an adverse influence on the effect of the invention, so that the case is not preferable.

Incidentally, the crosslinked gelatin support in the invention may be not only a single particle of the crosslinked gelatin as described above but also a particle aggregate obtained by aggregation of a plurality of particles thereof and the average particle diameter in this case may be from 25 to 2,000 μm, preferably from 50 to 1,700 μm, further preferably from about 60 to about 200 μm.

In the crosslinked gelatin support of the invention obtained as above, for controlling the adsorbed amount of the physiologically active substance as mentioned later, it is important that, in the case where zeta potential is measure in ethanol, the value falls within a range of −3 to −50 mV. Preferably, the value is preferably controlled to a range of −10 to −40 mV. When the zeta potential exceeds −3 mV, the resulting crosslinked gelatin support is electrically close to a neutral state, the performance of adsorbing the physiologically active substance is weakened, and thus there is a case where a sufficient adsorbability is not obtained. On the other hand, when the potential is less than −50 mV, the control of zeta potential of the resulting crosslinked gelatin support becomes unstable, there is a tendency that the crosslinked gelatin support having a stable performance is difficult to obtain, and as a result, there is a case where an objective effect possessed by the adsorbed and retained physiologically active substance cannot be sufficiently exhibited.

The zeta potential in the invention is measured as follows. After a dried particulate crosslinked gelatin support is weighed so as to be 1 mg/ml, it is suspended with 10 ml of ethanol (special grade reagent), and the suspension is diluted 100-fold with ethanol of a special grade reagent. Then, a value measured for the resulting diluted suspension at 25° C. using a zeta potential measurement device is taken as zeta potential in the invention. As the zeta potential measurement device, use can be made of commercially available devices such as a zeta potential•particle size distribution measurement device (manufactured by Beckman Coulter, Inc., trade name: DelsaNano), a zeta potential•particle diameter measurement system (manufactured by Otsuka Electronics Co., Ltd., trade name: ELSZ-1000ZS), a zeta potential measurement device (manufactured by Malvern Company, trade name: Zetasizer Nano), an ultrasonic particle size distribution•zeta potential measurement device (manufactured by Nihon Rufuto Co., Ltd., trade name: DT1202), a zeta potential measurement device for surface analysis (manufactured by Anton Paar GmbH, trade name: SurPASS), and the like. As measurement principles of these devices, there are adopted a laser Doppler multi-point detecting electrophoresis method, a laser Doppler method (dynamic electrophoresis light-scattering method), a phase analysis light-scattering method, an ultrasonic oscillating current method, a streaming potential•streaming current measurement method, and the like but any principle may be used.

It is preferable that the crosslinked gelatin support of the invention is one subjected to the decomposition treatment after a gelatin support is subjected to the crosslinking treatment as mentioned above and is one in which the content of water-soluble matter in the crosslinked gelatin support before the decomposition treatment is controlled to from 15 to 50% by weight and the content of water-soluble matter in the crosslinked gelatin support after the decomposition treatment is controlled to from 25 to 75% by weight. In this regard, it is also possible to make the water-soluble matter present by performing the crosslinking treatment alone without performing the decomposition treatment so that the content of the water-soluble matter is controlled to a range of 25 to 75% by weight. However, the water-soluble matter in this case is not a water-soluble matter formed by the decomposition treatment but a residual part of low-molecular weight gelatin which is not involved in the crosslinking treatment, and thus the effect of the invention cannot be sufficiently exhibited. Therefore, in the invention, it is important to control the content of the water-soluble matter before and after the decomposition treatment. Incidentally, with regard to the water-soluble matter in the invention, a main component thereof is gelatin but is not limited thereto and means any water-soluble matter eluted into purified water when the crosslinked gelatin support is immersed in purified water at 30° C. for 6 hours under standing.

Namely, in the invention, crosslinking between gelatin molecules and in the molecule takes place through crosslinking of gelatin and, thereafter, by the decomposition treatment of the resulting crosslinked gelatin, not the crosslinking is disconnected but the crosslinked gelatin molecule is cleaved, so that the molecular chain of the gelatin subjected to the crosslinking treatment is cleaved into small pieces. As a result, it is supposed that molecules showing water solubility are increased, even if they are derived from crosslinked gelatin, by generation of functional groups exhibiting water solubility, such as a carboxyl group, at the decomposition end part of the gelatin molecular chain. Furthermore, it is supposed that the adsorbed amount can be increased through replacement of the water-soluble matter with a physiologically active substance by the increase in water-soluble gelatin in the crosslinked gelatin support.

In the case where the content of the water-soluble matter in the gelatin support after the crosslinking treatment (before the decomposition treatment) is less than 15% by weight in the invention, since an excessive crosslinking treatment has occurred, the biodegradability is remarkably decreased, the biodegradability cannot be sufficiently regulated even when the decomposition treatment is performed. As a result, there is a possibility that a sufficient ability of controlled release of the physiologically active substance cannot be obtained. On the other hand, in the case of exceeding 50% by weight, water-insolubilization by the crosslinking treatment becomes insufficient and the biodegradability is exceedingly increased. Furthermore, since the biodegradability tends to be enhanced by the decomposition treatment, there is a tendency that a term for which controlled release of the physiologically active substance can be achieved is exceedingly shortened. Also, the gelatin support is dissolved in a dilution medium such as physiological saline in the preparation at time of use and hence there is a concern that the desired effect cannot be obtained.

Furthermore, in the case where the content of the water-soluble matter in the gelatin support after the decomposition treatment is less than 25% by weight, as a result of increased hydrophobicity owing to excessive crosslinking in the finally obtained crosslinked gelatin support, adsorption performance of the physiologically active substance is weakened and also the biodegradation rate is retarded, so that the controlled release of the physiologically active substance so as to exhibit the desired effect tends to be difficult to take place. On the other hand, when the content of the water-soluble matter exceeds 75% by weight, in the case where the support is administrated into a living body as a support for controlled release containing the physiologically active substance adsorbed thereon, there is a tendency that the biodegradation rate is fastened and the ability of controlled release is not exhibited.

The crosslinked gelatin support of the invention can afford a support for controlled release of a physiologically active substance, which permits the control of the amount of a physiologically active substance to be adsorbed and retained by utilizing its surface negative charge controlled to a specific range of zeta potential and controlling the content of the water-soluble matter and exhibits a desired effect. The physiologically active substance to be used in the invention is not particularly limited but, for example, use can be made of various drugs to be used for the purpose of treating various diseases by administration into the body, cytokines represented by interferon and interleukin, various growth factors (proliferation factors), and the like.

The above support for controlled release of a physiologically active substance is one in which the physiologically active substance is adsorbed and retained on the surface and/or inside of the support and which achieves controlled release of the adsorbed and retained physiologically active substance by administration into a living body to exhibit a desired effect. Examples of a method for administration into a living body include a method of suspending and dispersing the support in a solvent such as physiological saline and subsequently injecting the suspended and dispersed one intramuscularly in a local part of the living body to gradually achieve controlled release of the drug, a method of injection and administration into a blood vessel in the vicinity of an affected part of a disease so as to embolize the blood vessel to achieve the controlled release of the adsorbed physiologically active substance after embolization, and the like. In the case of performing these administration methods, a known device such as a catheter in addition to a syringe for injection can be used.

As a method for preparing the support for controlled release of a physiologically active substance in the invention, for example, the crosslinked gelatin support can be dispersed and filled together with the physiologically active substance into a syringe and adsorbed. Besides, there can be employed embodiments such as a case where the crosslinked gelatin support alone is filled into a syringe beforehand and physiological saline is sucked into the syringe at time of use to disperse the crosslinked gelatin support, or a case where the crosslinked gelatin support is filled into a vial, physiological saline is charged at time of use to disperse the crosslinked gelatin support, and the dispersion is sucked into a syringe, i.e., so-called preparation at time of use.

Incidentally, the crosslinked gelatin support administrated into a living body achieves controlled release of the adsorbed and retained physiologically active substance with gradual biodegradation thereof in the living body. The biodegradation time can be regulated by controlling the crosslinking conditions under which the crosslinked gelatin support is obtained and, as a result, a time for controlled release of the physiologically active substance can be controlled. Specifically, in the case where the time for controlled release is set to about 2 weeks in a muscle, the heating conditions in the step of crosslinking gelatin are preferably from 100 to 180° C. and from 1 to 24 hours. Incidentally, in the crosslinking step, since a heating operation is conducted, it is preferable to perform the crosslinking step under reduced pressure or under an inert gas atmosphere for suppressing the influence of oxygen in the case where there is a concern that the crosslinked gelatin support is oxidized and degenerated.

EXAMPLES

The following will describe the invention more specifically with reference to Examples. However, the invention should not be construed as being limited to the description of Examples and various modifications can be made in the range without departing from the technical ideas.

Example 1

After 5 g of gelatin (derived from swine skin, jelly strength: 100 g (in accordance with JIS K6503)) was dissolved in 100 ml of water at 40° C., it was filled into a plastic vessel. The aqueous gelatin solution was allowed to stand under a temperature of 2 to 10° C. for 17 hours to achieve gelling and subsequently frozen at −80° C. Then, the frozen one is dried under a vacuum of 10 kPa or less in a freeze drier to obtain a sheet-shaped product. The product was crushed in a crushing mill and the particle diameter was adjusted using sieves of 25 μm, 63 μm, and 1,700 μm to obtain gelatin crushed particles having average particle diameters of 25 μm or less and 63 to 1,700 μm.

Next, each of the gelatin particles is subjected to a heating treatment at 150° C. (±5° C.) for 4 hours in a state of rotation at a rate of 18 times per minute under vacuum (5 kPa or less) in a small-size drum vacuum drier (manufactured by Aichi Electric Co., Ltd., trade name: BHR-0.5 type) to obtain a crosslinked gelatin support of the invention.

Example 2

A crosslinked gelatin support was obtained in the same manner as in Example 1 except that, in Example 2, the heating treatment was performed at 170° C. (±5° C.) for 4 hours.

Example 3

After the crosslinked gelatin support obtained in Example 1 was placed in a plastic vessel under normal pressure in the air and was packaged with aluminum, it was irradiated with 25 kGy of γ-ray to obtain a crosslinked gelatin support subjected to the decomposition treatment.

Comparative Example 1

A crosslinked gelatin support subjected to the γ-ray irradiation treatment (decomposition treatment) was obtained in the same manner as in Examples 1 and 3 except that the temperature for the heating treatment was changed to 160° C. (±5° C.) in Comparative Example 1.

Among the crosslinked gelatin supports obtained in above Examples and Comparative Example, those having an average particle diameter of 25 μm or less were used for zeta potential measurement and those having an average particle diameter of 63 to 1,700 μm were used for measurement of the adsorbed amount of a physiologically active substance. The results are shown in Table 1 and FIG. 1. Incidentally, in the operation for measurement of the adsorbed amount, after the crosslinked gelatin support was impregnated with the physiologically active substance, the support was suspended in physiological saline, the portion not adsorbed in the crosslinked gelatin support was recovered as a supernatant, and it was used as a solution for measurement. In order to avoid mixing of a fine powder into the solution for measurement, the crosslinked gelatin having an average particle diameter of 63 to 1,700 μm was used for the measurement of the adsorbed amount.

The zeta potential of each of the crosslinked gelatin supports as the above products of Examples and Comparative Example and the adsorbed amount of the physiologically active substance were measured by the following methods.

<Measurement of Zeta Potential>

Each of the crosslinked gelatin supports as the above products of Examples and Comparative Example were made a dried state and, after one having an average particle diameter of 25 μm or less was weighed so as to be 1 mg/ml, it was diluted 100-fold with ethanol (a special grade reagent) and suspended. The resulting suspension was measured at 25° C. using a zeta potential•particle size distribution measurement device (manufactured by Beckman Coulter, Inc., trade name: DelsaNano).

<Measurement of Adsorbed Amount of Physiologically Active Substance>

Using a growth factor having a molecular weight of about 17,000 and a pigment having a molecular weight of 319.85 (methylene blue) as physiologically active substances, the adsorbed amount in the crosslinked gelatin support was measured as follows.

<Measurement of Adsorbed Amount of Growth Factor>

A growth factor as a physiologically active substance was dissolved in physiological saline so as to be a concentration of 0.14 mg/ml to prepare an aqueous physiologically active substance solution. For calibration curve, the aqueous physiologically active substance solution was diluted so as to be concentrations of 0.028 mg/ml, 0.056 mg/ml, 0.084 mg/ml, 0.11 mg/ml, and 0.14 mg/ml.

For measurement of the adsorbed amount of the growth factor as a physiologically active substance, each of the crosslinked gelatin supports as the products of Examples and Comparative Example was weighed in an amount of 0.025 g each. Then, the aqueous physiologically active substance solution having a concentration of 0.14 mg/ml was added to the crosslinked gelatin support in an amount of 0.35 ml each and the whole was allowed to stand at 40° C. for 1 hour so that the aqueous solution spread all over the crosslinked gelatin support as far as possible. Thereafter, 0.65 ml of physiological saline was added, a supernatant was filtered through a filter paper, and absorbance of the supernatant was measured on a high performance liquid chromatography. From the calibration curve prepared beforehand, the concentration of the physiologically active substance in the supernatant was determined and an adsorption ratio was calculated with taking an initial amount of the added physiologically active substance as 100%.

<Measurement of Adsorbed Amount of Pigment (Methylene Blue)>

Methylene blue as a physiologically active substance was dissolved in purified water so as to be a concentration of 0.5% by weight to prepare an aqueous physiologically active substance solution. For calibration curve, the aqueous physiologically active substance solution was diluted so as to be concentrations of 0.00005% by weight, 0.00025% by weight, 0.00050% by weight, and 0.00075% by weight.

For measurement of the adsorbed amount of the pigment as a physiologically active substance, each of the crosslinked gelatin supports as the products of Examples and Comparative Example was weighed in an amount of 0.04 g each. Then, the aqueous physiologically active substance solution having a concentration of 0.05% by weight was added to the crosslinked gelatin support in an amount of 0.5 ml each and the whole was allowed to stand at room temperature for 1 hour so that the aqueous solution spread all over the crosslinked gelatin support as far as possible. Thereafter, 4.5 ml of purified water was added, a supernatant was filtered through a filter paper, and absorbance of the supernatant was measured on an absorbance measurement device. From the calibration curve prepared beforehand, the concentration of the physiologically active substance in the supernatant was determined and an adsorption ratio was calculated with taking an initial amount of the added physiologically active substance as 100%.

TABLE 1

|  | Example 1 | Example 2 | Example 3 | Comparative Example 1 |
|---|---|---|---|---|
| Crosslinking temperature (° C.) | 150 | 170 | 150 | 160 |
| Crosslinking time (hr.) | 4 | 4 | 4 | 4 |
| Irradiation quantity of γ-ray (kGy) | 0 | 0 | 25 | 25 |
| Zeta potential (mV) | −20 | −3 | −48 | −51 |
| Adsorbed amount of growth factor (%) | 41.3 | 7.9 | 79.3 | 69.3 |
| Adsorbed amount of methylene blue (%) | 93.7 | 98.5 | 76.5 | 93.8 |

As is apparent from the results in Table 1 and FIG. 1, it is understood that, when the zeta potential of the crosslinked gelatin support surface falls within the range of −3 to −50 mV, the adsorption ratio (adsorbed amount) of the physiologically active substance is regularly varied according to increase and decrease in the zeta potential. Therefore, it is obvious that the desired effect can be exhibited by varying the zeta potential of the crosslinked gelatin support surface depending on the purpose of the physiologically active substance to be adsorbed and retained on and/or inside the crosslinked gelatin support.

Incidentally, in order to obtain a crosslinked gelatin support having a zeta potential in ethanol of more than −3 mV, the heating temperature at the time of crosslinking the gelatin support was controlled to 180° C. or higher but yellowing of the gelatin support became severe and thus the support was not suitable for the embolization use and the use for controlled release of a physiologically active substance as the uses of the invention. On the other hand, in the product of Comparative Example 1 in which the zeta potential in ethanol was less than −50 mV, the adsorbed amount of the physiologically active substance decreased as compared with that of the product of Example 3, so that it was impossible to obtain a crosslinked gelatin support which sufficiently satisfied the performance of the crosslinked gelatin support of the invention.

Examples 4 to 18

After the crosslinked gelatin support having an average particle diameter of 63 to 1,700 μm subjected to the crosslinking treatment after sieving in Example 1 was filled into a plastic vessel under normal pressure in the air and the vessel was packaged with aluminum, it was subjected to γ-ray irradiation to obtain a crosslinked gelatin support subjected to the decomposition treatment.

Conditions for the thermal crosslinking and conditions for the γ-ray irradiation are shown in Table 2.

Figure 2:
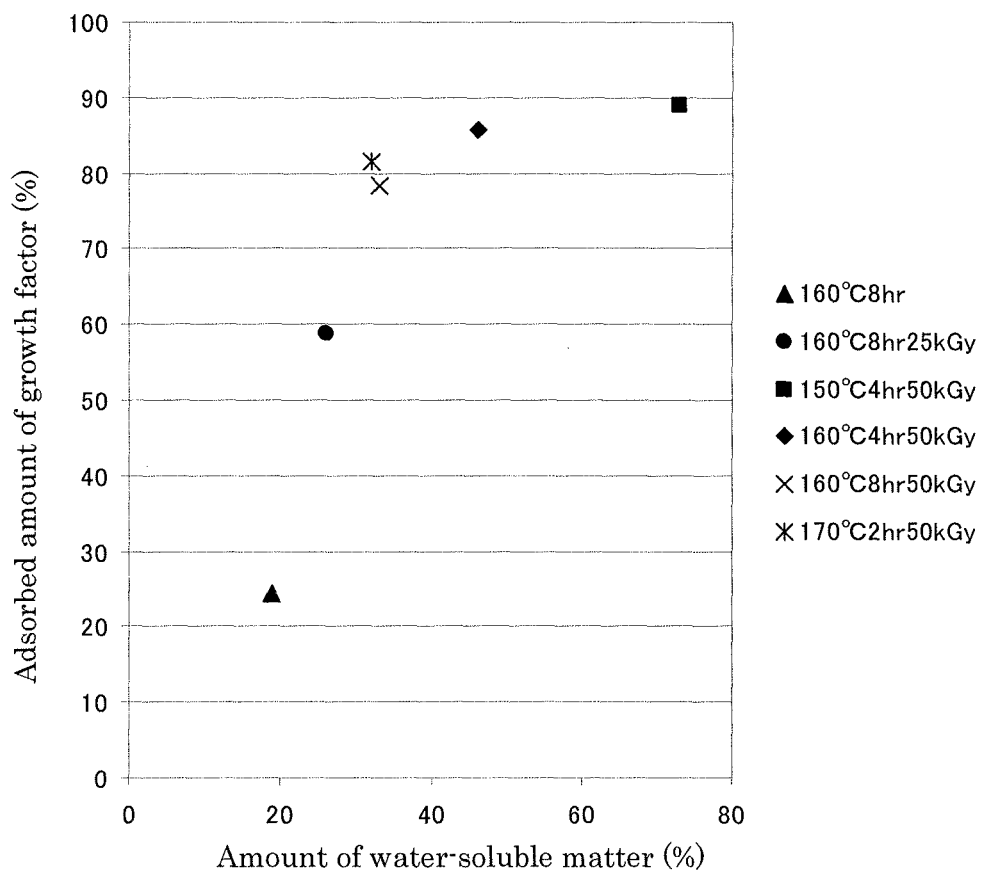
FIG. 2 is a graph showing relationship between the amount of water-soluble matter in the crosslinked gelatin support obtained in each of Experimental Examples and the adsorbed amount of growth factor as a physiologically active substance

For the crosslinked gelatin supports subjected to the decomposition treatment obtained as mentioned above, the content of the water-soluble matter in the support and the adsorbed amount of the physiologically active substance were measured by the following methods and the measurement results are shown in Table 2 and FIG. 2. Incidentally, in the measurement of the content of the water-soluble matter and the adsorbed amount of the physiologically active substance, in order to avoid mixing of a fine powder into the solution for measurement, the crosslinked gelatin having an average particle diameter of 63 to 1,700 μm was used.

<Measurement of Content of Water-soluble Matter>

Each crosslinked gelatin support in a dry state was weighed in an amount of 0.04 g and, after 5 ml of purified water was added thereto, the whole was allowed to stand at 30° C. for 6 hours. After a lapse of 6 hours on standing, natural filtration was performed through a filter paper having a pore diameter of 10 μm, the weight of which had been measured beforehand, and a residual solid matter on the filter paper was washed with 2 to 3 ml of purified water. After the filter paper and the residual solid matter were dried and weighed, the weights of the filter paper and the residual solid matter were subtracted from the weights of the crosslinked gelatin support and the filter paper before the test, and the water-soluble matter was calculated according to the following equation with taking the crosslinked gelatin support before the test as 100% by weight.

Amount of water-soluble matter (%)={1−(Weight of residual solid matter dried after test)/(Weight of crosslinked gelatin support before test)}×100

<Measurement of Adsorbed Amount of Physiologically Active Substance, Measurement of Adsorbed Amount of Growth Factor, and Measurement of Adsorbed Amount of Pigment (Methylene Blue)>

Measurements were performed in the same manner as mentioned above.

TABLE 2

| | No. | Crosslinking temperature (° C.) | Crosslinking time (hr.) | Irradiation quantity of γ-ray (kGy) | Amount of water-soluble matter (% by weight) | Adsorbed amount of growth factor (% by weight) | Adsorbed amount of pigment (% by weight) |
|---|---|---|---|---|---|---|---|
| Example | 4 | 150 | 4 | 0 | 42 | 46.2 | 93.7 |
| | 5 | 150 | 4 | 25 | 62 | 81.7 | 76.5 |
| | 6 | 150 | 4 | 50 | 73 | 88.8 | 69.2 |
| | 7 | 160 | 4 | 0 | 29 | 33.3 | 97.8 |
| | 8 | 160 | 4 | 25 | 39 | 74.2 | 93.8 |
| | 9 | 160 | 4 | 50 | 46 | 85.7 | 90.0 |
| | 10 | 160 | 8 | 0 | 19 | 24.4 | 98.4 |
| | 11 | 160 | 8 | 25 | 26 | 58.7 | 96.1 |
| | 12 | 160 | 8 | 50 | 33 | 78.3 | 94.2 |
| | 13 | 170 | 2 | 0 | 17 | 25.0 | 98.1 |
| | 14 | 170 | 2 | 25 | 37 | 67.6 | 95.4 |
| | 15 | 170 | 2 | 50 | 32 | 81.4 | 92.5 |
| | 16 | 170 | 4 | 0 | 22 | 20.7 | 98.5 |
| | 17 | 170 | 4 | 25 | 30 | 22.8 | 96.7 |
| | 18 | 170 | 4 | 50 | 33 | 21.9 | 95.5 |

From the results in Table 2 and FIG. 2, it is obvious that the content of the water-soluble matter in the crosslinked gelatin support is increased by the γ-ray irradiation and also the adsorbed amount of the growth factor as a physiologically active substance tends to be increased. Moreover, as is apparent from FIG. 2, when the content of the water-soluble matter in the crosslinked gelatin support after the decomposition treatment falls within the range of 25 to 75% by weight, the adsorbed amount of the physiologically active substance tends to increase as the water-soluble matter in the crosslinked gelatin support increases. However, when the content exceeds 75% by weight, since the adsorbed amount reaches close to 100%, it is understood that a large change in the adsorbed amount is not expected.

Incidentally, in Examples 16 to 18 in Table 2, although the amount of the water-soluble matter is changed by the presence or absence of the γ-ray irradiation and the variation of the irradiation quantity, the adsorbed amount of the growth factor is not so varied. The reason is considered as follows: Since the thermal crosslinking at 170° C. for 4 hours is performed and hence the crosslinking is more tightly achieved as compared with the products of other Examples, a water-soluble matter is formed but the influence of the water-soluble matter on the adsorption of the physiologically active substance decreases even when the crosslinked gelatin is decomposed by the irradiation with γ-ray. From the reason, it is understood that such a crosslinked gelatin support obtained under severe crosslinking conditions is effective for the case of preparing a support for controlled release in which the adsorbed amount of a physiologically active substance is suppressed.

Furthermore, as compared with the growth factor that has a relatively high molecular weight, with regard to the adsorbed amount of the pigment that has an extremely small molecular weight, since it is adsorbed to the crosslinked gelatin support for a short period of time, the adsorbed amount thereof is too large as compared with the adsorption of the growth factor, so that no difference appears among individual products of Examples. This is remarkable in the cases of Examples 7 to 18 in which variation in the amount of the water-soluble matter is small even when conditions are changed. Incidentally, in Examples 4 to 7 in which the amount of the water-soluble matter is relatively large and the variation thereof is also large, the pigment adsorbed to the water-soluble matter is eluted and transferred into purified water together with the water-soluble matter at the measurement of the adsorbed amount of the pigment, so that the variation in the measurement of the adsorbed amount becomes large.

As above, in the case where the crosslinked gelatin support is utilized as a support for controlled release of a physiologically active substance, it is obvious that the control of the adsorbed amount becomes possible by thermally crosslinking gelatin and further controlling the content of the water-soluble matter after the decomposition treatment to 25 to 75% by weight and, as a result, it becomes possible to regulate the time for controlled release and the amount of controlled release of the physiologically active substance.

The present application is based on Japanese Patent Applications No. 2013-089142 filed on Apr. 22, 2013 and No. 2013-089143 filed on Apr. 22, 2013, the entire contents thereof being hereby incorporated by reference.

What is claimed is:

1. A crosslinked gelatin support, wherein a surface of a crosslinked gelatin is negatively charged and has a zeta potential in ethanol of from −3 to −50 mV;
   wherein the crosslinked gelatin has been further subjected to a decomposition treatment; and
   wherein a content of water-soluble matter in the crosslinked gelatin before the decomposition treatment is from 15 to 50% by weight and is increased to 25 to 75% by weight after the decomposition treatment.

2. The crosslinked gelatin support according to claim 1, wherein the crosslinked gelatin is thermally crosslinked.

3. The crosslinked gelatin support according to claim 1, wherein the decomposition treatment is a γ-ray irradiation treatment.

4. The crosslinked gelatin support according to claim 1, wherein the crosslinked gelatin support is a single particle having a non-porous structure or a particle aggregate thereof.

5. A support for controlled release of a physiologically active substance comprising: the crosslinked gelatin support according to claim 1; and
   a physiologically active substance adsorbed and retained on and/or inside the crosslinked gelatin support; wherein the physiologically active substance is at least one selected from the group consisting of drugs, cytokines and growth factors.

* * * * *